United States Patent [19]
Larsen et al.

[11] Patent Number: 5,888,966
[45] Date of Patent: Mar. 30, 1999

[54] PROCESS FOR SEPARATING MILK CLOTTING ENZYMES, AND STABLE RENNET COMPOSITIONS

[75] Inventors: Robert Larsen, Virum; Marianne Kirsten Harboe, Lyngby; Pål Martin Ladsten, Copenhagen, all of Denmark

[73] Assignee: CHR. Hansen A/S, Denmark

[21] Appl. No.: 737,089

[22] PCT Filed: Apr. 25, 1995

[86] PCT No.: PCT/DK95/00171

§ 371 Date: Dec. 12, 1996

§ 102(e) Date: Dec. 12, 1996

[87] PCT Pub. No.: WO95/29999

PCT Pub. Date: Nov. 9, 1995

[30] Foreign Application Priority Data

May 3, 1994 [DK] Denmark .................... 0505/94

[51] Int. Cl.⁶ .................... A61K 38/43; C07K 1/14
[52] U.S. Cl. .................... 514/2; 514/21; 530/350; 530/412; 530/414; 530/416; 530/418; 424/94.66
[58] Field of Search .................... 530/412, 416, 530/418, 414, 350; 514/2, 21; 424/94.66

[56] References Cited

U.S. PATENT DOCUMENTS

| | | | |
|---|---|---|---|
| 3,763,010 | 10/1973 | Schleich | 195/63 |
| 3,950,221 | 4/1976 | Kokusho et al. | 195/65 |
| 4,721,673 | 1/1988 | Uren et al. | 435/183 |
| 5,151,358 | 9/1992 | Heinsohn et al. | 435/226 |

FOREIGN PATENT DOCUMENTS

| | | |
|---|---|---|
| 147376B | 7/1984 | Denmark . |
| 091664 | 10/1983 | European Pat. Off. . |
| 137710 | 4/1985 | European Pat. Off. . |
| 230231 | 7/1987 | European Pat. Off. . |
| 61-185186 | 8/1986 | Japan . |
| 106521 | 4/1983 | United Kingdom . |
| A2106521 | 4/1983 | United Kingdom . |
| WO 88/02220 | 4/1988 | WIPO . |
| WO 90/15866 | 12/1990 | WIPO . |

OTHER PUBLICATIONS

Subramanian, S., "Separation of chymosin and pepsin in calf rennet by dye–ligand affinity chromatography", Preparative Biochemistry, vol. 17, No. 3, pp. 297–312 (1987).

*Primary Examiner*—Cecilia J. Tsang
*Assistant Examiner*—Anish Gupta
*Attorney, Agent, or Firm*—Hunton & Williams

[57] ABSTRACT

A process of separating milk clotting enzymes in extracts of animal stomach tissue which comprises contacting a partially purified extract with an ion exchange resin under conditions where chymosin is bound to the resin and recovering the chymosin, the process optionally comprising the further step of recovering pepsin, from a pepsin-rich extract fraction using an ion exchange resin, and a liquid of powdered rennet composition containing at least 90% of its milk clotting activity as chymosin activity, the composition comprising a chymosin stabilizing agent which is typically selected from a protein, a peptide, an amino acid or ascorbic acid.

46 Claims, No Drawings

PROCESS FOR SEPARATING MILK CLOTTING ENZYMES, AND STABLE RENNET COMPOSITIONS

FIELD OF INVENTION

The present invention relates to the manufacturing of milk clotting enzymes, in particular to the manufacturing of rennet compositions containing a high proportion of chymosin and to rennet compositions in which the milk clotting enzyme has been stabilized.

TECHNICAL BACKGROUND AND PRIOR ART

Milk clotting enzymes are widely used in the cheese industry to provide a curd of the major milk proteins. Commercially available milk clotting enzymes include native enzymes derived from microbial or animal tissue sources, or the enzymes may be provided as gene products of recombinant cells expressing a milk clotting enzyme of animal or microbial origin.

Native milk clotting enzymes of animal origin are isolated by extraction from animal tissues containing one or several of these enzymes. Thus, animal milk clotting enzymes include several enzymes of the group of aspartic endopeptidases having molecular weights which are in the range of about 35,000 to 42,000 daltons (group 3.4.23 according to the Enzyme Nomenclature, 1992 of the International Union of Biochemistry and Molecular Biology, IUBMB) such as pepsin A (3.4.23.1) and gastricsin (3.4.23.3) which is excreted into the gastric juice of vertebrates including ruminants, pigs and humans, and chymosin (3.4.23.4) which is a predominantly neonatal gastric enzyme with high milk clotting activity, excreted in mammals. The molecular weights of animal milk clotting enzymes are in the range of about 35,000 to about 42,000 daltons. Thus, chymosin has a calculated molecular weight of 35,652 daltons.

The primary industrial source of native animal milk clotting enzymes are stomachs of calves and adult cattle in which essentially all of the in-vivo milk clotting activity is associated with the presence in the gastric juice of chymosin and pepsin A. However, when produced in the stomach tissue cells, these enzymes occur as enzymatically inactive pre-enzymes which are designated pre-prochymosin and pre-pepsinogen A, respectively. When chymosin is excreted, an N-terminal fragment is cleaved off to give prochymosin including a pro-fragment. Prochymosin is an essentially inactive form of the enzyme which, however, under acidic conditions becomes activated to the active chymosin molecule by removal of the pro-fragment. This activation takes place in-vivo in the gastric lumen under appropriate pH conditions. Pepsinogen A is activated into the active enzyme by partial hydrolysis under acidic conditions.

Pseudochymosin is the designation of a chymosin species where only part of the pro-fragment (amino acid residues 1–27) is removed. Pseudochymosin will e.g. occur in an extract which has been exposed to a low pH, such as a pH of 2. Pseudochymosin has enzyme activity and is stable at low pH but is processed to chymosin at higher pH. The isoelectric point of pseudochymosin is not known, but it is assumed to be higher than 4.9.

Recently, animal chymosin that is produced in recombinant microorganisms including filamentous fungi has been introduced into the industrial market. Such recombinantly manufactured milk clotting enzyme products are also referred to as fermentation produced chymosin or rennet.

In addition to the above milk clotting enzymes of animal origin several natively produced microbial enzymes are used in the dairy industry. Such enzymes are referred to as microbial milk clotting enzymes or microbial coagulants in the following. Examples of such enzymes include Rhizomucor (previously Mucor) miehei proteases including destabilized, i.e. oxidized *Rhizomucor miehei* protease, *Mucor pusillus* protease and *Endothia parasitica* protease.

Preparations or compositions containing native milk clotting enzymes of animal origin are prepared industrially by extraction from stomach tissues, in particular from ruminants including calves and adult cattle. Enzyme-containing crude extracts contain chymosin species including precursors, and pepsin species in ratios which depend primarily on the age of the animal. Thus, the distribution between chymosin and pepsin in stomachs from young calves is typically about 80:20 to 90:10 whereas in stomachs from adult cattle it is typically about 25:75. It will be understood that intermediate distributions between these enzyme species may be found in older calves and young cattle. As an example, the above ratio in extracts from these animals is typically in the order of 50:50.

Conventionally, commercial products containing milk clotting enzymes of animal origin is manufactured by a multistep, time consuming process which typically include the following steps: (i) preparing a crude enzyme-containing extract by extracting comminuted, frozen or dried calf or cattle stomachs with water, (ii) transforming the proenzymes into the active enzymes, (iii) a clarification step wherein a flocculant is added to facilitate the subsequent filtration step, (iv) concentration steps, (v) repeated clarification, (vi) further filtration step to remove precipitated impurities, (vii) adjusting salt and preservative concentration, (viii) adjusting the enzymatic strength and composition to obtain the finished product which is usually referred to as rennet. Prior to packaging, the rennet product may be subjected to a final filtration step including a sterile filtration. This conventional process of manufacturing rennet involves a high consumption of chemical agents and energy.

The entire conventional process of rennet manufacturing may take about one week. It will be understood that such conventionally manufactured enzyme preparations will contain a mixture of chymosin and pepsin, the latter enzyme being much less active than chymosin in respect to milk clotting.

However, chymosin is considered in the dairy industry as far the best milk clotting enzyme for manufacturing of cheese with respect to specific clotting activity, curd formation, cheese texture and flavour and yield of cheese. The distribution of milk clotting enzymes, i.e. the composition of a given batch of animal rennet may vary considerably depending i.a. on the animal stomach raw material. If a conventional rennet having a relatively high proportion of chymosin is desired, stomachs from young calves is the preferred raw material. Such products may be designated calf rennet. Rennet products having lower proportions of chymosin may be manufactured on the basis of stomachs from older calves or from adult cattle (ox rennet). Naturally, rennet products having intermediate enzyme chymosin content may be obtained e.g. by mixing a calf rennet and an ox rennet. The strength of a crude extract as described above is typically in the range of 5 to 30 Chr. Hansen units (CHU) /mL as defined below. Typically conventionally manufactured commercial liquid rennet products has an enzymatic strength in the range of 40 to 100 CHUs/mL.

The above conventional rennet manufacturing process has several essential drawbacks. Firstly, the process is time consuming and labour-intensive; secondly, the provision of rennet having high contents of chymosin requires use of stomachs from young calves which is a relatively scarce and costly raw material; thirdly, the process requires use of clarifying agents which add to the production costs; fourthly part of the process takes place at pH values where microbial growth is not inhibited, which may cause spoilage problems and furthermore, part of the process is at pH values where the chymosin has a reduced stability; fifthly, the process results in large quantities of contaminated waste-water and sixthly, the resulting rennet may be less suitable as the basis for production of powdered rennet products with a very high milk clotting activity due to its relatively low enzymatic activity (strength) and finally, it is a significant drawback that the liquid rennet products have low strengths which implies significant transportation costs.

In the prior art some of the above problems have been addressed e.g. by suggesting processes whereby chymosin and pepsin are separated. Thus, WO 88/02220 discloses a method for separating chymosin from a liquid containing chymosin and pepsin, comprising adjusting the enzyme-containing liquid to a pH of about 3.8 to about 5.2, preferably in the range of 4.4 to 4.5, and to a conductivity of about 2 to about 19 mS/cm, and contacting this liquid with an equilibrated anion exchange medium to bind pepsin, recovering the chymosin in the liquid resulting after contact with the exchange medium and removing the pepsin from the exchange medium. However, this process results in a fraction where chymosin is present in an amount which is generally lower than that of the starting enzyme-containing liquid and the process is based on anion exchange at a pH where chymosin is unstable and which allows microbial growth. Furthermore, the anion exchange medium as disclosed is a weak DEAE-cellulose ion exchanger the performance of which under the disclosed conditions will be affected by small variations in the pH or conductivity of the extract applied to the weak exchanger.

In WO 90/15866 is disclosed a method of recovering chymosin from an aqueous solution which additionally contains pepsin, comprising adding to the aqueous solution, polyethylene glycol (PEG) and an inorganic salt so as to form a two-phase system which after separation into a chymosin and pepsin-rich PEG phase and an enzyme-poor salt phase, and contacting the PEG phase with an ion exchange resin under conditions where the chymosin is bound to the resin, and recovering the chymosin from the resin. Although this process may result in a rennet product essentially only containing chymosin, it involves several technological drawbacks which contribute significantly to the production costs: (i) the use of PEG during the process requires strict measures be taken to remove the PEG, (ii) PEG and inorganic salt in the high amounts to be used are costly, (iii) in order to dissolve the added salt, it is required to use energy to warm the solution, (iv) the two phases must be separated by centrifugation (v) after the ion exchange step, the PEG must either be recycled or discharged, and (vi) according to that disclosure it is necessary to regenerate the resin after each batch.

The present invention provides a novel one-phase ion exchange-based process of separating chymosin and pepsin from a crude extract of animal tissues containing these milk clotting enzymes that is surprisingly efficient with regard to separating and concentrating the enzymes and to obtaining a high yield of enzymes, and which in comparison to the prior art methods is simple and cost-effective.

However, it has been found that rennet products containing milk clotting enzymes of animal origin that are provided by an ion exchange process may be prone to reduction in their enzymatic activity, assumingly due to oxidation of certain amino acid residues. This phenomenon of oxidative enzyme destabilization is known in the art in connection with microbial coagulants, and is in fact utilized in the manufacturing of so-called destabilized milk clotting proteases of microbial origin, which is oxidized to a level where they are readily inactivated during the pasteurization of the whey. It is also known to add stabilizing agents to such proteases in order to preserve their activity up to their use. Thus, DE 3234761 discloses solutions of such fungal proteases stabilized by the addition of at least 0.1 wt % methionine.

Milk clotting enzymes may e.g. be exposed to oxidizing agents such as e.g chlorine or cleaning agent residues present in the water used during the manufacturing of rennet products or in the dairies. In contrast to the rennet products provided herein, conventionally manufactured animal milk clotting enzyme extracts (rennets) are not very sensitive to oxidation due to their high content of impurities which are readily oxidized.

It has now surprisingly been found that it is possible to protect animal milk clotting enzymes having a low content of impurities by the addition of compounds which are readily oxidized, including methionine. Therefore, it is an important aspect of the present invention to provide liquid and powdered rennet products comprising a milk clotting enzyme and a stabilizing compound which improve the stability of the enzymes against oxidative inactivation. In the present context, rennet products having a low content of impurities include rennets manufactured on the basis of enzyme-containing animal tissues, e.g. in accordance with the process of this invention or by an other process leading to a rennet product with a low content of impurities which are readily oxidizable, and milk clotting enzymes expressed by a recombinant microorganism (fermentation product rennets).

SUMMARY OF THE INVENTION

Accordingly, the present invention relates in a first aspect to a process of separating milk clotting aspartic endopeptidases present in an extract of animal stomach tissue, comprising the steps of (i) preparing an aqueous extract of animal stomach tissue that contains the aspartic endopeptidases chymosin and pepsin, and/or their pro-enzymes, to obtain a one-phase, crude and particulate matter-containing extract comprising said endopeptidases, (ii) adjusting the pH in the extract to a value where the pro-enzymes are converted into active endopeptidases, and keeping the extract at this pH until essentially all of the pro-enzymes are activated, (iii) separating particulate matter from the extract resulting from step (ii) to obtain a one-phase, partially purified aqueous extract containing the milk clotting endopeptidases essentially in their active forms, (iv) mixing the partially purified extract of step (iii) with an ion exchange resin under conditions where pseudochymosin chymosin and chymosin present in the extract, is bound to the resin, (v) separating the mixture of (iv) into the ion exchange resin with chymosin and pseudochymosin bound thereto and an extract fraction containing substantially all of the pepsin also present in the partially purified extract resulting from step (iii), (vi) recovering, under conditions where essentially all pseudochymosin is converted into chymosin, the chymosin and pseudochymosin from the ion exchange resin into an aqueous medium to obtain a solution containing substantially all of the chymosin and pseudochymosin present in the partially purified extract resulting from step (iii) as chymosin.

In further aspects, the present invention pertains to a liquid rennet composition and a powdered rennet composition, respectively in which at least 90% of the milk clotting activity is from chymosin, comprising a chymosin stabilizing agent.

DETAILED DISCLOSURE OF THE INVENTION

Presently, most milk clotting enzyme-containing rennet products on the market is animal rennet, primarily manufactured by extracting the enzymes from stomachs of calves (calf rennet) and adult cattle (ox rennet), although pig stomachs may also be used as raw material. The major milk clotting enzymes in animal rennet are, as it is explained above, the highly active chymosin and the less active pepsin, the distribution of which enzymes in a given rennet product varies according to the age of the animals from which the stomach raw material is derived.

Clearly, much more adult cattle raw material for rennet production is available than calf stomachs. However, there is a considerable industrial interest in utilizing the cheaper and more abundant raw material from cattle for the production of rennet products with a high content of chymosin relative to that of pepsin. One way of achieving this is to separate chymosin and pepsin present in an aqueous extract of stomach tissues of ruminant origin.

Accordingly, the present invention provides in one aspect a process whereby a separation of milk clotting aspartic endopeptidases present in an extract of animal stomach tissue is achieved. As used herein the term "aspartic endopeptidase" is related to the enzyme nomenclature of the IUBMB, 1992 as referred to above.

In a first step of this process a crude, one-phase particulate matter-containing aqueous extract comprising said endopeptidases and/or their pro-enzymes is prepared by subjecting comminuted animal stomach tissue material to an extraction procedure e.g. as described below. However, this extraction step is, in contrast to the conventional method of preparing rennets, carried out without the addition of compounds increasing the conductivity, i.e. salts, acids or bases in order to obtain an extract having a conductivity which is in the range of 1 $\mu$S/cm to 30 mS/cm. Accordingly, the extraction medium may conveniently be tap water or water with a reduced content of naturally occurring ions such as deionized or distilled water.

The extraction procedure normally includes one or more steps of extracting the tissue at a temperature which is typically in the range of 0° to 30° C., under agitation for at least 10 to 100 minutes in a suitable volume of water. An auxiliary bulking agent may be added during extraction in order to facilitate the separation of the crude extract from the tissue. Following each cycle of extraction, coarse particulate matter of the extraction suspension is separated by subjecting the suspension to a pressing treatment using any suitable pressing equipment, resulting in an enzyme-containing press liquor containing particulate matters which are not removed by the pressing step. The extraction procedure may be repeated, and the press liquors resulting from each cycle is finally combined, resulting in a crude aqueous extract of the stomach tissue, comprising a substantial part of the milk clotting aspartic endopeptidase species hereof.

In a subsequent step, the pH of the extract is adjusted to a value which is in the range of 0.5 to 5.0 whereby the pre-enzymes are converted into active endopeptidases. A preferred pH value is one in the range of 1.0 to 3.0, such as in the range of 1.5 to 2.5 including a pH of about 2.0. The adjustment of the pH is conveniently obtained by the addition of a strong inorganic acid such as $H_2SO_4$, HCl, $H_3PO_4$, $HNO_3$ or an organic acid such as e.g. acetic acid, formic acid or lactic acid. The extract is kept at the low pH for a period of time which is sufficient to achieve an activation of essentially all of the pre-milk clotting enzymes. This activation period is generally in the range of 10 to 120 minutes, preferably in the range of 20 to 60 minutes such as about 30 minutes. It should be noted that a proportion of the activated chymosin is present as pseudochymosin as defined above, the proportion hereof depending i.a. on the pH.

The enzymatic activity of the resulting activated, crude extract varies i.a. according to the animal raw material and to the volume of extraction medium, but is typically in the range of 5 to 30 CHU/mL, the highest activity being present in extract of stomach tissues from young animals. It is preferred that the resulting crude, partially purified extract has a low ionic strength and accordingly, the process is preferably one resulting in an extract that has a conductivity which is in the range of 1 $\mu$S/cm to 50 mS/cm, preferably in the range of 1 $\mu$S/cm to 30 mS/cm, such as in the range of 1 to 20 mS/cm.

Following the above activation step, the crude low pH-extract is subjected to a step whereby at least part of the particulate matters present herein is separated from the aqueous medium. Such particulate matters include stomach tissue particles, coagulated proteins and cell agglomerates deriving from the stomach raw material, and particles of any auxiliary agent used during the extraction cycle(s). This separation may be obtained by any conventional industrial separation method, such as e.g. filtration, centrifugation or sieving. The efficiency of the separation step is greatly enhanced by the low pH of the crude extract, since most of the impurities present herein are in a precipitated state at this pH and accordingly, a degree of purification is achieved by this simple process step which is at least comparable to that obtained by the above conventional clarification procedure The supernatant or filtrate resulting from this separation step is a one-phase, partially purified aqueous extract containing the extracted milk clotting chymosin and pepsin species which essentially are in their enzymatically active forms.

The separated particulate matters whether as a filter cake, a sieving residue or as a concentrate resulting from centrifugation, may contain a certain amount of milk clotting enzyme activity and accordingly, the process may suitably include one or more additional steps of washing the separated particulate matters in order to recover at least part of this enzyme activity, and the washings may, if desired, be added to the above aqueous extract.

The thus obtained, partially purified extract is then subjected to a step whereby the chymosin is separated from the pepsin A by contacting the extract with an ion exchange resin under conditions where chymosin species including chymosin and pseudochymosin present in the extract, are bound to the resin. In the present context, the term ion exchange resin denotes a resinous material which binds charged compounds electrostatically and includes ion exchange resins that are prepared of insoluble materials such as e.g. agarose, poly-acrylamide, cellulose or derivatives thereof including carbo-xymethyl cellulose, or glass, that contain negatively charged ligands, e.g. sulfoxyethyl, sulfopropyl, phosphate moieties, —$CH_2COO^-$, —$C_3H_6SO_3^-$, or positively charged ligands, e.g. quaternary amine moieties, diethylaminoethyl (DEAE) moieties or diethylamino, covalently bound to the insoluble resinous material. Negatively charged resins bind cations and are known as cation exchangers or cation exchange resins. Similarly, positively charged resins bind anions and are referred to as anion exchangers or anion exchange resins. The two major milk clotting enzymes to be separated, i.e. chymosin and pepsin A have different isoelectric points (i.p.). That of chymosin is in the range of 4.5 to 5.1 whereas as bovine pepsin A has an i.p. of about 2.0. Accordingly, chymosin will be positively charged at pH values below the i.p. and may therefore be bound to a cation exchanger at pH values below the i.p. whereas the pepsin A at a pH of about 2 or higher will be either uncharged or negatively charged. Therefore, the present process includes contacting the above crude extract with a suitable cation exchanger at a pH which is below the i.p. for chymosin such as in the range of about 2 to a pH not exceeding the i.p.

In accordance with the invention, a preferred cation exchange resin is one which has a constant high degree of ionization across a wide pH range, such as a pH range of 1 to 13 charge including a pH range of 2 to 12. Such an ion exchanger may be referred to as a strong ion exchanger, a significant characteristic of such an exchanger being that its performance is less sensitive to variations in pH and conductivity.

In preferred embodiments of the invention, a cation ion exchange resin having a high binding strength is used in the enzyme separation step. In the present context, the term "high binding strength" indicates that the ion exchange resin has a high degree of ligand substitutions. In the art, such resins are generally considered to be particularly suitable for separation of smaller molecules having molecular weights below 30,000 daltons, such as peptides, or for separating biopolymers of almost identical charge (e.g. in high resolution chromatography). Due to the high binding strengths of such resins it is also contemplated in the art that enzymes may be bound so firmly to an ion exchange resin of a high binding strength that it is difficult to have enzyme molecules bound to such a resin released herefrom without impairing the enzymatic activity. Therefore, resins having a high binding strength have not hitherto been used successfully for purification of enzymes for any significant purposes.

According to the invention, a particularly useful cation exchanger may be selected from a sulfoxyethyl (SE) ion exchanger such as Whatman® SE cellulose cation exchangers. Such SE cation exchangers may have specific characteristics including the degree of SE substitutions which determines the binding strength, and the structural dimensions determining the size of molecules which is preferentially bound. It is generally considered in the art that ion exchangers of high binding strengths are particularly useful when two or more proteins having isoelectric points (i.p.'s) close to each other are to be separated.

As an example, the Whatman® SE 52 cation exchanger is described by the manufacturer as a moderately substituted ion exchanger showing high protein capacity and as being particularly suitable for binding of proteins having molecular weights greater than 30,000 daltons whereas the Whatman® SE 53 cation exchanger is described as a strong cation exchanger that is specially designed for the binding of smaller biopolymers with molecular weights up to 30,000 daltons and is therefore according to the manufacturer, ideal for the separation of e.g. peptides, interferons and interleukins.

However, it was unexpectedly and surprisingly found that the Whatman® SE 53 ion exchanger was much more effective in selectively binding chymosin than was the corresponding SE 52 ion exchanger, regardless of the fact that the molecular weight of chymosin is greater than 30,000. Furthermore, it was surprising that the separation of chymosin and bovine pepsin A having very different i.p.'s were so effective as it was found. It was particularly surprisingly found that chymosin bound to the above SE 53 cation exchanger was readily elutable without loss of activity regardless of the very high binding strength of that cation exchanger. Therefore, a Whatman® SE 53 or any other cation exchanger having similar functional characteristics represents one particularly useful cation exchanger in the process according to the invention.

The amount of the cation exchanger relative to the amount of extract applied thereto is generally in the range of 0.1:100 to 10:100 in terms of the weight ratio between the ion exchange resin and the extract, the range preferably being 0.2:100 to 8:100 such as 0.5:100 to 5:100.

The contact between the cation exchanger and the enzyme-containing extract may be performed as a batch process or by a process where the ion exchanger is contained in a suitable column and letting the extract flow through this column. For industrial scale processes, a batch process may be advantageous, since it is more convenient and less costly than a column process, significant advantages including more convenient washing of the ion exchange resin, less risk of having pH gradients in the contact mixture and significantly shorter production time. When using a batch process, the mixture of ion exchange resin and extract is preferably agitated during the contact in order to obtain an effective contact between these reagents. The contact time is suitably in the range of 5 to 120 minutes, such as in the range of 10 to 60 minutes, e.g. in the range of 15 to 45 minutes.

The conductivity of the partially purified extract to be contacted may have a negative effect on the binding of chymosin to the cation exchanger, but it has been found that a conductivity up to about 30 mS/CM has an insignificant negative effect on the binding.

Following the above step of binding chymosin to a cation exchange resin, the extract-ion exchanger mixture is separated into the ion exchange resin with chymosin and pseudochymosin bound thereto, and an extract fraction containing substantially all of the pepsin also present in the partially purified extract. This separation may be carried out in accordance with any industrially suitable separation method such as filtration, centrifugation, settling/decanting or sieving. The separated ion exchange particles may be washed one or several times, e.g. with deionized water and the washing(s) may be added to the above pepsin-containing fraction.

It has surprisingly been found that a separated ion exchange resin can be re-contacted with one or several further volumes, such as up to 5 to 10 further volumes, of the acidified, partially purified extracts without any regeneration and/or equilibration procedures.

Subsequent to each cycle of contacting a volume of enzyme-containing extract with the ion exchange resin, the chymosin and/or pseudochymosin molecules bound to the resin is recovered under conditions where essentially all pseudochymosin is converted to chymosin, into an aqueous elution medium to obtain a solution containing substantially all of the chymosin and pseudochymosin present in the partially purified extract as chymosin.

A suitable elution medium is a buffered salt solution having 10 a pH exceeding the i.p. for chymosin. Accordingly, the pH of the elution medium is preferably at least about 4.5, such as in the range of about 5 to about 8, preferably in the range of 5.5 to 7.0, including the range of 5.6 to 6.0. The salt is e.g. NaCl, and the concentration of the salt is typically in the range of 0 to 30% (w/v) such as in the range of 2 to 25%, e.g. in the range of 4 to 15%. The buffering agent may suitably be selected from a phosphate, an acetate or any other buffering agent having buffering capacity in the pH range of 4 to 8. The concentration of the buffering agent is typically in the range of 0.01M to 1M, e.g. 0.05M phosphate.

In preferred embodiments of the invention the process as defined herein is one wherein at least 90% of the milk clotting activity recovered in the elution step is chymosin activity, such as at least 95% of the milk clotting activity including at least 98% chymosin activity, e.g. at least 99% chymosin activity.

The volume of the elution medium relative to the volume of extract that is contacted with the ion exchange resin determines the enzymatic activity (the strength) of the resulting chymosin-containing eluate and accordingly, the volume of elution medium is selected so as to obtain a suitable strength. For many practical purposes a high strength of the eluate is desirable and although a wide range of ratios between the volume of elution medium and that of the extract applied to the ion exchange resin is within the scope of the invention, particularly interesting ratios are within a range of 1:1 to 1:20, preferably within the range of 1:2 to 1:15 such as within the range of 1:3 to 1:10.

It will be understood that the selection of a desirable range of ratios also depends on the strength of the partially purified starting extract. As one example, a ratio of about 1:5 may be useful when the extract is made from calf stomaches, since the resulting enzymatic strength in the eluate typically will be in the range of 50 to 100 CHU/mL which may be a convenient strength of a commercial liquid rennet product. Such concentrates of rennet may contain an amount of chymosin activity that is increased relative to the starting crude extract by a factor which is in the range of 2 to 10000, such as in the range of 10 to 1000, including the range of 20 to 500.

It may, as it is mentioned above, be of considerable commercial interest to provide rennet products having a high enzymatic strength. Such concentrated products can be transported at a low cost to the location of use and the rennet concentrate may, if desired, be diluted subsequently to any preferred strength.

A high activity rennet product may in accordance with the invention also be provided by a process as defined herein which as a further step comprises a removal of water from the chymosin-containing eluate whereby a chymosin-containing preparation is provided which is at least partially dehydrated. Such a dehydration may conveniently be obtained by ultrafiltration of the chymosin-containing preparation resulting in a retentate containing substantially all of the chymosin present in the retentate. Retentates may be obtained having strengths which are in the range 50 to 10,000 CHUs/mL, e.g. a strength in the range of 100 to 8000 CHUs/mL including a strength of 500 to 5000 CHUs/mL.

It is known in the art that rennet products with increased activity relative to simple extract-based products, based on conventionally prepared aqueous extracts of animal stomachs, may be provided by precipitating proteins in the extract, including the milk clotting enzymes. However, such conventional high chymosin rennet products will contain a mixture of chymosin and pepsin dependent on the raw material and on the precipitation conditions.

A retentate prepared as described above may be used for milk clotting purposes as is, or there may be added usual rennet additives to the retentate to obtain a liquid concentrated rennet composition e.g. having a strength of at least 50 CHUs/mL such as at least 100 CHUs/mL, including a strength of at least 200 CHUs/mL such as 1000 CHUs/mL, preferably at least 1500 CHUs/mL, more preferably at least 2000 CHUs/mL, most preferably at least 2500 CHUs/mL and in particular at least 3000 CHUs/mL.

In accordance with the invention, a powdered rennet product can be obtained by subjecting a concentrated eluate or a retentate as defined above to a drying step to obtain a rennet powder. This drying step may be performed by any drying process which is suitable for drying of proteins including as examples spray drying, vacuum drying, air drying or freeze-drying. It may be advantageous to add a solid compound such as NaCl to the retentate prior to the drying. A rennet powder prepared in accordance with the present invention may e.g. have a strength of at least 100 CHUs per g, preferably at least 200 CHUs per g, more preferably at least 500 CHUs per g, even more preferably at least 800 CHUs per g and in particular at least 1000 CHUs per g such as at least 1500 CHUs per g, e.g. at least 2000 CHUs per g.

In accordance with the invention the step of recovering the chymosin from the cation exchange medium by elution preferably results in an eluate wherein at least 90% of the milk clotting enzymes is chymosin, more preferably at least 92%, even more preferably at least 95%, most preferably at least 97%, in particular at least 98%, such as at least 99% or even at least 99.5%.

It has, as it is also explained above, been found that purified chymosin-containing preparations such as those resulting from the above process may be susceptible to oxidative reductions in enzymatic activity and accordingly the invention encompasses a process which includes the addition of a compound which can protect the chymosin against such activity reductions. In the present context, such compounds are referred to as chymosin stabilizing agents. In accordance with the invention such agents may be incorporated into a chymosin-containing rennet product by being added during the above process, e.g. to the crude or the partially purified aqueous extract or to the chymosin-containing eluate or to a rennet preparation obtained by at least partial removal of the water of the eluate.

In the present context, a suitable stabilizing agent may be selected from a protein, a polypeptide, an amino acid including methionine and cysteine, a non-nitrogen antioxidant compound such as ascorbic acid or an ascorbate. Particularly useful stabilizing agents include DL methionine and L-methionine. A preferred chymosin stabilizing agent is one which, when added during the process in an amount which results in an amount in the finished rennet product of the agent which is in the range of 0.01 to 10 wt % has a stabilizing effect whereby the stabilized rennet product retains an activity which is higher than that of the same product without added stabilizing agent when the product is diluted in distilled water containing 20 ppm of chloramine T to an activity of 4 CHUs/mL and kept herein at room temperature for about 60 minutes. Preferably at least 50% of the activity is retained, e.g. at least 75%, such as at least 90% of the activity, e.g. at least 95% of the activity or even at least 97% of the activity including at least 98% of the activity.

It is an interesting aspect of the present invention that the relatively low pepsin milk clotting activity of the above pepsin-containing fraction resulting from the separation of the ion exchange resin from the mixture of the partially purified extract and the resin may be utilized to prepare commercially interesting rennet products.

The strength of this fraction after separation (the starting strength) is typically in the range of 1 to 20 CHUs/mL. In addition to pepsin the fraction contains a substantial amount of other proteins originating from the stomach raw material, and accordingly it is difficult to concentrate the pepsin by an ultrafiltration process. It has been found that the starting enzymatic strength may in accordance with the invention be increased by a factor which is in the range of 10 to 10,000 by subjecting the fraction to a further step of contacting it with an ion exchange resin under conditions where substantially all of the pepsin is bound to the resin, and recovering the pepsin from the resin into an amount of a liquid medium which is less than the amount of extract fraction applied to the resin. The contacting conditions include a pH value where the pepsin (and any residual chymosin from the cation exchange step) binds to an anion exchange resin as defined above.

It was found that an anion exchange resin having a high binding strength was not only particularly effective with regard to binding of pepsin, but also allowed an effective elution of the bound enzyme. One such useful anion exchange resin is Whatman® DE 53.

The pepsin-containing fraction is contacted with the resin at a pH which is typically in the range of about 5 to about 7, either in a batch process or by applying the fraction to a column containing the anion exchange resin. In a batch process the mixture of the anion exchange resin and pepsin-containing fraction is preferably agitated during the contact in order to obtain an effective contact between these reagents. The contact time is suitably in the range of 5 to 120 minutes, such as in the range of 10 to 60 minutes, e.g. in the range of 15 to 45 minutes.

Following the above contact step the anion exchange resin is separated in accordance with any industrially suitable separation method such as filtration, centrifugation, settling/decanting or sieving. The separated ion exchange particles may be washed one or several times, e.g. with deionized water and the washing(s) may be added to the liquid phase resulting from the separation. A separated anion exchange resin can be re-contacted with one or several further volumes, such as up to 5 to 10 further volumes, of the pepsin-containing fraction without any regeneration and/or equilibration procedures.

Subsequent to each cycle of contacting a volume of pepsin-containing fraction with the ion exchange resin, pepsin molecules bound to the resin is recovered into an aqueous elution medium to obtain a solution containing substantially all of the pepsin present in the above fraction.

A suitable elution medium is a buffered salt solution having a pH which is preferably in the range of 5 to 7, including the range of about 5.5 to about 6.5. The salt is e.g. NaCl, and the concentration of the salt is typically in the range of 1 to 30% (w/v), such as in the range of 2 to 25%, e.g. in the range of 4 to 15%. The buffering agent may suitably be selected from a phosphate, a citrate, an acetate or any other buffering agent which under the elution conditions have a buffering capacity. The concentration of the buffering agent is typically in the range of 0.01M to 1M, e.g. 0.05M phosphate.

The present invention relates in one aspect to a rennet composition comprising a chymosin stabilizing agent, in which at least 90% of the milk clotting activity is from chymosin, In accordance with the invention the composition may be a liquid composition or it may be in the form of a powdered rennet composition. In accordance with the invention, the stabilizing agent as defined herein may, as it is described above, be added during the above process of separating the milk clotting enzymes as present in an extract of animal tissues, or it may be added to a finished chymosin-containing rennet preparation e.g. containing other rennet additives. In one preferred embodiment the composition is one in which at least 95% of the milk clotting activity is from chymosin such as at least 97% of the activity, e.g. at least 98% of the activity including a composition in which at least 99% of the milk clotting activity is from chymosin. The milk clotting activity which is not from chymosin may be from an other aspartic endopeptidase as defined herein or it may be from a milk clotting enzyme of microbial origin as also defined hereinbefore.

The composition is preferably one which retains at least 50% of its milk clotting activity when it is diluted in distilled water containing 20 ppm of chloramine T to an activity of 4 CHUs/mL and kept herein at room temperature for about 60 minutes. More preferably the composition is one wherein, under these conditions at least 75% of the activity is retained, such as at least 90% of the activity. Particularly preferred embodiments include compositions wherein at least 95% of the activity is retained, e.g. at least 97% of the activity, including at least 98% of the activity.

The stabilizing agent is selected from the compounds as mentioned above, a preferred stabilizing agent being selected from methionine including DL methionine or L-methionine. It has unexpectedly been found that a methionine even in very small amounts such as less than 0.1 wt % has an excellent stabilizing effect on purified chymosin. Accordingly, the invention provides in one embodiment a stabilized chymosin-containing composition comprising methionine, the amount hereof typically being in the range of 0.01 to 2 wt %. Even with an amount of methionine in the range of 0.01 to 0,09 wt % a stabilizing effect is observed whereby 90 to 100% of the activity is retained after contacting the composition with chloramine under the above test conditions.

The stabilized chymosin-containing rennet composition as defined above may have any commercially useful strength. However, in advantageous embodiments the compositions may have a milk clotting activity of at least 20 CHUs per g or mL, preferably at least 50 CHUs per g or mL such as at least 100 CHUs per g or mL, preferably at least 200 CHUs per g or mL, more preferably at least 500 CHUs per g or mL, most preferably at least 800 CHUs per g or mL, and in particular at least 1000 CHUs per g or mL.

In useful embodiments, the rennet composition is a high activity or concentrated composition containing at least 1100 CHUs per g or mL, preferably at least 1500 CHUs per g or mL, more preferably at least 2000 CHUs per g or mL, most preferably at least 2500 CHUs per g or mL, and in particular at least 3000 CHUs per g or mL. Such high activity rennet compositions may either be liquid compositions e.g. provided by ultrafiltration of a chymosin-containing eluate as defined above or such compositions may be based on concentrated mammal chymosin expressed in a recombinant microbial cell (fermentation produced rennet).

Therefore, in useful embodiments of the invention, the chymosin of the composition is chymosin derived from a mammal stomach tissue such as separated chymosin prepared in accordance with the process of separating milk clotting aspartic endopeptidases as defined herein. In further useful embodiments the chymosin is be a mammal chymosin expressed in a microbial cell. Host cells comprising a gene coding for the mammal chymosin can suitably be selected from bacterial species including *E. coli,* a yeast species such as from Saccharomyces or Klyuveromyces spp. or a fungal species, e.g. selected from an Aspergillus sp., a Mucor sp. or a Penicillium sp.

Furthermore, the invention encompasses chymosin-containing compositions which contain a mixture of a mammal chymosin extracted from stomach tissues and a mammal chymosin expressed by a recombinant microbial host cell.

The stabilized chymosin-containing composition may further comprise usual rennet additives such as carrier substances including salts, e.g. NaCl or preserving agents.

The invention is further illustrated in the below examples.

EXAMPLES

Materials and methods

A. Determination of rennet strength (Analytical procedure AP 001 of Chr. Hansen's Laboratorium)

(i) Assay principle

The strength of a rennet is determined as a milk clotting activity. Following the addition of diluted rennet to a standard milk substrate, the milk will flocculate. The milk clotting time is the time from addition of the rennet until formation of visible flakes in the milk substrate. The strength of a rennet sample is found by comparing the milk clotting time for the sample to that of a standard rennet preparation, a normal. It is important that the normal has the same composition of enzymes as that of the sample.

As the method is intended to be used for rennets of bovine origin, i.e. calf rennet, bovine rennet and mixtures hereof, the enzymes in question are chymosin and bovine pepsin. Normals containing these two enzymes can be blended in the correct proportions from the liquid normals: (i) the calf rennet normal and (ii) the bovine rennet normal.

(ii) Standard assay conditions

Substrate: Reconstituted skim milk, pH 6.5, adjusted with $CaCl_2$, cf. item (vi) below Temperature: 32° C.±0.2° C. in a thermostatic water bath Enzyme addition: To 25 mL of the reconstituted skim milk is added 0.5 mL of enzyme solution sample, diluted to give a clotting time in the range of 380 to 500 seconds.

(iii) Activity units

Rennet strength is given in Christian Hansen units (CHU)/mL or CHU/g. A calf rennet standard powder and a bovine rennet standard powder have been defined as having a specific strength. All liquid and powder standard preparations (normals) are referred to these powder standards.

1 CHU/mL in the diluted enzyme solution of the calf rennet standard (normal) will when properly diluted under the above standard conditions give a clotting time of 410 to 460 seconds, i.a. depending on skim milk powder used, and including day-to-day variations.

1 CHU/mL in the diluted enzyme solution of the bovine rennet standard (normal) will under the above standard assay conditions give a clotting time which is 20–25% below that of the above calf rennet standard. This has been defined because of the greater sensibility of the bovine pepsin to the $Ca^{2+}$ content in milk. At a pH in cheese milk which is about 6.6, 1 CHU of the two types of standards will give essentially the same clotting time.

(iv) Enzyme standards (normals)

Primary standards

The system of enzyme standards comprises the below primary standards in powder form which are kept at −18° C. in evacuated ampoules:

(a) calf rennet powders comprising about 90% chymosin and about 10% bovine pepsin (batch KNP III, 322 CHU/g; batch KNP IV, 303 CHU/g; batch KNP V, 311 CHU/g), (b) bovine rennet powder comprising about 25% chymosin and about 75% bovine pepsin.

Secondary standards

As secondary standards are used liquid normals which are kept at a temperature of 0°–4° C., including:

(a) calf rennet normal containing 90%±2% of chymosin and 10%±2% of bovine pepsin and having a strength of 50±1 CHU/mL, (b) bovine rennet normal containing 25%±2% chymosin and 75%±2 bovine pepsin.

The composition of the above standards of rennet of bovine origin is based on activity percentages determined as described in the below modified Garnot assay procedure. All of the standards are produced by Chr. Hansen's Laboratory, Copenhagen, Denmark.

(v) Reagents (a) Sodium acetate buffer, pH 5.5, ionic strength 0.08: 10 mL of 1M $CH_3COOH$ and 10 g of $CH_3COONa$, 3 $H_2O$ is dissolved in glass distilled water up to 1000 mL;

(b) Calcium chloride solution, 50% (w/v): 662.4 g of $CaCl_2$, 2 $H_2O$ p.a. is dissolved in glass distilled water up to 1000 mL, and the solution is degassed under vacuum. The concentration is checked by titration with 0.01N EDTA solution;

(c) 0.05% (w/v) $CaCl_2$: 2.00 mL $CaCl_2$ and 1998 mL of glass distilled water or sterilized, demineralized water is mixed on the day where it is used;

(vi) Substrate

Reconstituted skim milk, pH 6.5 is prepared as follows: 110 g of low heat, spray dried skim milk powder is suspended in 1000 mL of 0.05% (w/v) $CaCl_2$. The milk solution is stirred for 30 minutes at room temperature, and then left for a further 30 minutes. The milk substrate is stored between 4° and 25° C. and for no longer than 3 hours. The pH of the milk is usually 6.48 to 6.52.

(vii) Preparation of diluted liquid normals and liquid samples

The calf rennet normal is diluted with acetate buffer pH 5.5 to contain 1 CHU/mL. The dilution is 50 times and can be obtained by using 2.0 calf rennet normal up to 100 mL. The bovine rennet normal is diluted with acetate buffer pH 5.5 in such a way that the clotting time obtained is the same as for the calf rennet normal±40 seconds. The dilution is normally 60 times and is e.g. obtained by using 2.5 mL bovine rennet normal and buffer up to 150 mL.

Preferably, all rennet samples to be assayed should be checked against a normal with about the same enzymatic composition as the sample. The diluted normals, both containing 1 CHU/mL, is mixed to contain the same amount of chymosin±5% as the sample. Samples containing more chymosin than the calf rennet normal are tested against the calf rennet normal. Samples containing less chymosin than the bovine rennet normal is tested against the bovine rennet normal.

Liquid rennet samples to be assayed are diluted with the above acetate buffer to give a clotting time corresponding to the relevant normal±40 seconds.

When samples of powdered rennet preparations are to be assayed, samples are diluted in acetate buffer to give a clotting time corresponding to that of the relevant normal±40 seconds.

(viii) Assay procedure 25.0 g of milk substrate is weighed or measured into a volumetric flask and the flask is preheated for 800 seconds±100 seconds to ensure both the correct temperature and the correct equilibrium of the milk salts as the concentration of $Ca^{2+}$ in the substrate is dependent on the temperature. The flasks are transferred to a rennet testing apparatus consisting of (i) a thermostated water bath at a temperature of 32° C.±0.2° C., (ii) 12 counters and (iii) device for rotating 12 volumetric glass flasks. 0.5 mL of an enzyme sample solution is quickly pipetted to a flask being rotated in the testing apparatus and simultaneously, a counter giving the time in seconds, is activated ($T_o$=0 seconds). When the milk film in the rotating flask is observed to become disrupted into small flakes or dots, the counter is stopped, and the milk clotting time, $T_s$, in seconds, is noted.

A sample and the corresponding normal must be tested in the same run to obtain the smallest possible variations in the testing conditions. A duplicate determination includes two dilutions of the sample and two dilutions of the normal. One diluted normal can be used as reference for several samples having similar enzymatic compositions.

(ix) Calculations

The enzymatic strength of a sample is calculated on the basis of each of the single determinations of clotting times and not based on the average values of clotting times. Finally, the strength of the sample is calculated as the average of the duplicate determinations.

The strength is calculated according to the below formula:

$$Strength = \frac{T_n \times Dil_s \times St_n}{T_s \times Dil_n}$$

where $T_n$=Clotting time in seconds for the normal
$T_s$=Clotting time in seconds for the sample
$Dil_n$=Dilution factor for the normal
$Dil_s$=Dilution factor for the sample
$St_n$=Strength of the normal, 50 CHU/mL B. Determination of content of chymosin and bovine pepsin in rennets by ion exchange chromatography (modified Garnot procedure) (Analytical procedure AP 122 of Chr. Hansen's Laboratorium)

(i) Principle

Following desalting of a rennet sample by dialysis, the two enzyme species chymosin and bovine pepsin are separated on an ion exchange column and collected in two fractions. The milk clotting activity of the two fractions are measured against the corresponding standards (normals) to give the composition expressed in percentages of enzyme species, based on determination of enzymatic strength in CHU determined as defined above.

This method is intended to be used for rennet preparations containing chymosin and bovine pepsin only. The presence of other commercially available milk clotting enzymes including porcine pepsin, *Rhizomucor miehei* proteases including destabilized *Rhizomucor miehei* protease, *Mucor pusillus* protease and *Endothia parasitica* protease will give misleading results, as all of the microbial enzymes will be eluted together with the chymosin in the first fraction, and the porcine pepsin will be eluted with the bovine pepsin A in the second fraction. Consequently, the absence of these enzymes of non-bovine origin should be checked using a suitable method such as the below rocket-immunoelectrophoretic method or the immuno-diffusion methods as described in the IDF (International Dairies Federation) standard method 110A, 1987. Rennets of bovine origin contain in addition to chymosin and bovine pepsin A, minor amounts of bovine gastricsin (about 5%, calculated on the content of bovine pepsin A). The bovine gastricsin fraction will primarily be eluted with the chymosin in fraction 1 as defined below.

(ii) Reagents (a) 0.025M piperazine buffer: 4.85 g of piperazine-hexahydrate is weighed into a beaker (A) and 42.8 g of 1M HCl is weighed into an other beaker and transferred quantitatively to beaker A followed by stirring until the salts are dissolved. The resulting solution is transferred quantitatively to a 1000 mL volumetric flask and glass distilled water is added to volume;

(b) 0.20M NaCL in 0.025M piperazine buffer, pH 5.3: 11.7 g of NaCl is dissolved in 1000 mL 0.02M piperazine buffer, pH 5.3;

(c) 0.50M NaCl in 0.025M piperazine buffer, pH 5.3: 29.2 g of NaCl is dissolved in 1000 mL 0.02M piperazine buffer, pH 5.3;

(d) ion exchange resin: Whatman® DE-52 or equivalent;

(e) about 0.5M piperazine solution: 97 g of piperazine-hexahydrate is dissolved in 1 liter of glass distilled water;

(f) the column material is prepared as follows: a thin slurry of the ion exchange resin is prepared by gentle swirling and the pH adjusted to about 5.3 by titration with a strong HCl solution (15–20% HCl). The slurry is allowed to settle followed by decanting the supernatant containing fines. If necessary, the ion exchange resin is redispersed in sufficient buffer to give a viscous, but fluid suspension. A few drops of toluene are added.

(iii) Assay procedure (a) Preparation of ion exchange column: the ion exchange resin suspension is warmed to room temperature and 15 mL of the gently swirled suspension is poured into each column (Pharmacia, 0.9×15 cm or equivalent). The ion exchanger is allowed to settle and the final height of material is in the range of 9 to 12 cm. The column is equilibrated with 100 mL of 0.025M piperazine buffer, pH 5.3 at a flow rate of 80 mL/h using a peristaltic pump. Each column may be used for analysis of up to 5 samples within one month form packing. Prior to each new run, the column is equilibrated with at least 100 mL of 0.025M piperazine buffer, pH 5.3 at the above flow rate.

(b) dialysis of rennet samples: dialysis tubing, size 8/32 is softened by immersion for a few minutes in water. The tubing is bound at one and 10 mL of sample is transferred to the tubing. When the sample is a liquid rennet preparation it is used as is, whereas a powdered rennet preparation is suspended in 0.025M piperazine buffer, acetate buffer as defined above or in water prior to transfer to the dialysis tubing. The 10 mL of rennet sample is dialysed against 500 mL 0.025M piperazine buffer in a measuring glass for at least 2 hours, preferably overnight. If kept overnight, the dialysis is under refrigeration, otherwise at room temperature.

(c) separation of enzymes: the column is run at room temperature 10 mL of the dialysed rennet sample is applied to the column. When the strength and approximate composition of the sample is known, an amount of dialysed sample giving about 1 CHU/mL in the weakest fraction, is applied. The amount of enzymes applied to the column should not exceed 600 CHU. The elution of enzymes is performed at a flow rate of 80 mL/h using (i) 0.20M NaCl in 0.025M piperazine buffer until 100 mL is collected in a volumetric flask (pool 1, the chymosin fraction) followed by the collection of 3 mL eluate in a test tube (intermediate fraction, should contain no enzymes), (ii) 0.5M NaCl in 0.025M piperazine buffer until 100 mL is collected in a volumetric flask (pool 2, the pepsin fraction). The collection of eluate is started simultaneously with the application of the sample.

(iv) Determination of milk clotting activity

The flasks containing the above eluates are shaken well before determination of milk clotting activities as described above. The first fraction (pool 1) is measured against the calf rennet normal, diluted with acetate buffer. The second fraction (pool 2) is measured against the bovine rennet normal. The milk clotting time for the intermediate fraction should exceed 1800 seconds.

(v) Calculations

The content of chymosin and bovine pepsin in activity percentages are calculated as follows:

$$\% \text{ chymosin:} \frac{St_{pool1} \times 100}{St_{pool1} + St_{pool2}}$$

$$\% BpA: 100 - \% \text{ chymosin}$$

$St_{pool\ 1}$ is the strength of pool 1 calculated as follows:

$$St_{pool1}: \frac{T_{KN} \times Dil_{pool1} \times St_{KN}}{T_{pool1} \times Dil_{KN}}$$

$T_{KN}$: the clotting time in seconds for the calf rennet normal $T_{pool\ 1}$: The clotting time in seconds for pool 1

$Dil_{pool\ 1}$: Dilution factor for pool 1

$Dil_{KN}$: Dilution factor for the calf rennet normal $St_{KN}$: Strength of the calf rennet normal, 50 CHU/mL $St_{pool\ 2}$ is the strength of pool 2 calculated as follows:

$$St_{pool2}: \frac{T_{ON} \times Dil_{pool2} \times St_{ON}}{T_{pool2} \times Dil_{ON}}$$

$T_{ON}$: the clotting time in seconds for the bovine rennet normal $T_{pool\ 2}$: The clotting time in seconds for pool 2

$Dil_{pool\ 2}$: Dilution factor for pool 2

$Dil_{ON}$: Dilution factor for the bovine rennet normal $St_{ON}$: Strength of the bovine rennet normal, 50 CHU/ML The standard deviation on a single determination is about 3%. absolute.

C. Quantification of enzyme components in rennet by Rocket Immunoelectrophoresis (RIE)

Quantitative determination of milk clotting enzyme species were made according to the RIE assay described in Rothe et al., 1976 (J. Dairy Res. 43, 85–95 and Rothe et al., 1977 (J. Dairy Res. 44, 73–77 (1977). This assay is based on the following principle:

The sample protein components are moved by electrophoretic force in a gel containing antibody monospecific to the protein antigen to be determined. Initially small soluble antigen-antibody complexes are formed, and during the movement these grow larger until they precipitate. The movement then stops, and—under specified conditions—the height of the precipitate curve ("the rocket height") is a function of the antigen amount in the sample.

The assay is applicable for the determination of enzyme species derived from mammals including bovine animals and pigs, and milk clotting enzymes natively expressed by micro-organisms such those mentioned above.

Example 1

Laboratory-scale column chromatography separation of chymosin and pepsin

A crude calf rennet extract was activated by adjusting the pH to about 2 and subsequently filtered to obtain a pH 2 filtered rennet extract. This extract was dialysed against a buffer (buffer A) of the following composition: 20 mM citric acid and 0.1% (w/v) Na-benzoate, pH 2.5, conductivity 2.3 mS/cm and 50 mL of the dialysed rennet having a strength of about 22 CHU/mL, a pH of 2.45 and a conductivity of 4.3 mS/cm was used in the following separation experiment.

2.5 g of Whatman® cation exchanger SE-53 (a sulfoxyethyl (SE) strong acid cation exchanger) was suspended in 25 mL of buffer A and packed in a 1×10 cm column (FPLC™, Pharmacia) followed by equilibration with 40 mL of buffer A. 50 mL of the above dialysed rennet was applied to the column (run No. 227 FPLC™, superloop) and elution was carried out with buffer B (FPLC™) having the following composition: 10% NaCl in 0.05M phosphate, pH 5.9, conductivity 114 mS/cm. 2 mL fractions were collected and analyzed for chymosin and pepsin by RIE according to the method described above, and for conductivity The results are summarized below:

TABLE 1.1

Separation of chymosin (Ch) and BpA by SE-53 column chromatography

| Fraction | Ch, CHU/mL | BpA, CHU/mL |
|---|---|---|
| 4 | <0.5 | 1.5 |
| 7 | <0.5 | 1.5 |
| 10 | <0.5 | 1.3 |
| 13 | <0.5 | 1.1 |
| 16 | <0.5 | 1.4 |
| 19 | <0.5 | 1.5 |
| 22 | <0.5 | |
| 25 | <0.5 | 1.5 |
| 28 | <0.5 | 1.4 |
| 30 | <0.5 | 0.1 |
| 31 | 0.16 | |
| 32 | 170 | 0.4 |

The above results show that the selected chromatography separation procedure was effective with regard to separation of chymosin and bovine pepsin.

Example 2

Comparison of different ion exchangers under different pH conditions in a laboratory-scale batch separation procedure The purpose of this experiment was to compare the effectiveness of different ion exchange resins in respect to separation of chymosin and BpA in a laboratory-scale batch procedure.

(i) selected pH conditions

The pH conditions were selected on the basis of the isoelectric points of chymosin (about 4.8) and of BpA ($\leq 2$). Further it was kept in mind that the chymosin in the extract which has only been exposed to pH 2 (without increasing the pH) is not only present as chymosin, but also as pseudo-chymosin for which the isoelectric point is not known with certainty tainty but it is assumed to be higher than 4.9.

(ii) ion exchange resins used

The following Whatman® ion exchange resins/pH values were used:

(i) Whatman® SE-53/2.5;

(ii) Whatman® DE-53 (DEAE cellulose tertiary base anion exchanger)/2.5;

(iii) Whatman® CM-52 (carboxymethylcellulose cation exchanger)/2.5;

(iv) Whatman® DE-53/4.6;
(v) Whatman® DE-52 (DEAE cellulose tertiary base anion exchanger/2.5;
(vi) Whatman® DE-52/4.5.

At pH 2.5 chymosin will be positively charged and BpA will be neutral or slightly negatively charged. At pH 4.5 chymosin will be neutral or slightly positively charged and BpA negatively charged.

(iii) buffers used

The following buffers for pH 2.5 were used: (a) buffer A containing 20 mM citric acid, 0.% (w/v) Na-benzoate, pH 2.5, conductivity 2.3 mS/cm, and (b) buffer B having the following composition: 10% (w/v) NaCl in 0.05M phosphate, pH 5.9, conductivity 114 mS/cm.

For pH 4.5, the following buffers were used: (c) buffer A containing 0.5% (w/v) Na-benzoate titrated to pH 4.5 and supplemented with NaCl to an electric conductance of 9 mS/cm, and (d) 10% (w/v) NaCl in buffer A, conductivity 112 mS/cm.

(iv) rennet preparations used

A portion of the pH 2 filtered rennet extract as used in Example 1 was dialysed overnight against buffer A, pH 2.5 to obtain a pH 2.5 rennet preparation having an electric conductance of 2.3 mS/cm. The pH 4.5 rennet preparation was prepared by increasing the pH of an aliquot of this preparation to 4.5. The conductivity of this pH 4.5 rennet was 4.2 mS/cm. Both of these rennet preparations contained 12 CHU/mL and the distribution of chymosin/BpA was about 91.2% /8.8%. Accordingly, each preparation had a total content of about 383 CHU chymosin and 37 CHU BpA, i.e. a total content of enzymatic activity of 420 CHU.

(v) procedure for batch separation procedure

The procedure comprised the following steps: (a) 1.00 g of each ion exchange resin was weighed into a 50 mL conical centrifuge tube provided with a cap, (b) the resins were equilibrated with 40 mL of the respective buffer A, followed by centrifugation and decanting, (c) the equilibration step was repeated, (d) 35 mL of rennet preparation was added to the respective ion exchange resins as outlined in the below table 2.1; the contents of the tubes were mixed by rotation for 20 minutes followed by centrifugation and decanting (fraction A, table 2.1), (e) the bound enzyme was eluted with 5.0 mL of the appropriate buffer B (fraction B, table 2.1), (f) the elution step (e) was repeated (fraction C) and finally (g) the fractions were analyzed for strength and enzyme composition.

The results as summarized below in table 2.1 illustrate that among the tested ion exchange resins and pH values, the most effective separation is obtained with SE-53 at pH 2.5.

DE-53 functions effectively for the chymosin fraction (A), but the corresponding BpA fraction (B) is not pure. Based on these results, SE-53 was selected for the following experiments.

TABLE 2.1

Comparison of various ion exchange media

| Ion Exchange Media | Trial pH | Charge of Ion Exchanger | Expected Realisation | Fraction A, Non-bound Enzyme | | Fraction B, 1st Eluate | | Fraction C, 2nd Eluate | Conclusion |
| --- | --- | --- | --- | --- | --- | --- | --- | --- | --- |
| | | | | Strength | % Ch/BpA | Strength | % Ch/BpA | Strength | |
| 1. SE-53 | 2.5 | – | Ch binds | 2.9 | 0/100 | 52.7 | 100/0 | 4.7 | Good function |
| 2. DE-53 | 2.5 | + | BpA binds | 12.2 | 58/42 | 3 | 57/43 | >0.5 | Bad function. The fractions are not pure |
| 3. CM-52 | 2.5 | – | Ch binds | 10.3 | 87/13 | 8.7 | 97/3 | 2.4 | Bad function |
| 4. DE-53+ | 4.5 | + | BpA binds | 8.7 | 100/0 | 16.6 | 48/52 | 1.2 | Functions partly |
| 5. DE-52+ | 2.5 | + | BpA binds | 11.3 | 84/14 | 2.6 | 71/29 | — | Function not satisfactory |
| 6. DE-52+ | 4.5 | + | BPA binds | 9.9 | — | 6.6 | — | — | Function is uncertain |

Example 3

The influence of the conductivity on the efficiency of Whatman® SE-53 in batch chromatography separation of rennet enzymes (i) rennet used The rennet starting material used was non-activated crude calf rennet extract prepared essentially as described in example 4 below using tap water as the extraction medium. The rennet extract was activated at pH 2 and filtered at this pH value (batch PS-36). A portion of the rennet was desalted in order to test the effect of low ion strength as well.

(ii) chromatography procedure (a) 0.71 g portions of SE-53 were equilibrated with 25 mL of buffer A, pH 2.5, followed by titration to pH 2.5, centrifugation and decanting, (b) 25.0 Ml of the rennet was added and the mixture left to stand for 20 minutes, followed by centrifugation and decanting (c) elution was carried out using 3.5 Ml of buffer B containing 25% (w/v) NaCl in 0.05M phosphate, Ph 6.1; the Ph was adjusted to 5.9 in the mixture and the ion exchange resin was separated by centrifugation.

The eluates from steps (b) and (c) were analyzed for strengths and it appears from the results summarized in table 3.1, that the efficiency of SE-53 chromatography was not affected significantly at conductivity values in the range of 2.3 to 27.5 Ms/cm, whereas at a value exceeding 30 Ms/cm the efficiency was reduced.

TABLE 3.1

The influence of the conductivity (mS/cm) on the efficiency of Whatman ® SE 53 cation exchanger

| Trial | Eluate | mS/cm | Not bound activity, CHUs/mL |
| --- | --- | --- | --- |
| A | 25 mL desalted extract[1] | 2.3 | 1.1 |
| B | 12.5 mL of A + 12.5 mL of C | 8.7 | 1.4 |
| C | 25 mL extract, non-desalted[2] | 12.5 | 2.8 |
| D | 25 mL of C + NaCl | 17.5 | 2.0 |
| E | 25 mL of C + NaCl | 22.5 | 2.4 |

TABLE 3.1-continued

The influence of the conductivity (mS/cm) on the
efficiency of Whatman ® SE 53 cation exchanger

| Trial | Eluate | mS/cm | Not bound activity, CHUs/mL |
|---|---|---|---|
| F | 25 mL of C + NaCl | 27.5 | 2.8 |
| G | 25 mL of C + NaCl | 33.0 | 5.2 |

[1]Strength: 8.6 CHUs/mL; pH 2.4
[2]Strength: 12.5 CHUs/mL; pH 2.2

Example 4

The preparation of an ion-exchanged calf rennet in semi-industrial scale

The purpose of this experiment was to prepare a high concentrate chymosin preparation.

1. Extraction and activation step 2500 calf stomachs were extracted twice at about 8° C. in water to obtain a total of about 8000 L of crude extract following separation of the press cake. These combined press liquors were subjected to an activation step by the addition of concentrated HCl to give a pH of 1.97.

To 3000 L of the thus activated crude extract 1.7% (w/v) of perlite filtering material was added and this mixture was filtered by means of a frame filter. The resulting filtrate was adjusted to pH about 2.0. The filter cake was suspended in 310 L of water, pH readjusted to about 2.0, and the filtration step repeated to give a combined, filtered extract volume of 2890 L of which 834 L was used in the further processing.

The filtrate had the following composition:

| | |
|---|---|
| Volume | 834 L |
| Conductivity | 11.4 mS/cm |
| Enzymatic activity | 14.9 CHU per mL |
| Total activity | 12.4 MCHU |
| pH | 2.06 |
| % activity from chymosin | 90 |

2. Ion exchange step A to separate chymosin and pepsin 2.0 kg of Whatman® SE 53 which is a microgranular pre-swollen strong acid sulfoxyethyl cation exchanger was suspended in about 200 L of filtrate under agitation for about 20 minutes followed by separation of the ion exchanger by filtration. The filtrate (the first pepsin fraction) was collected. This fraction had the following composition: volume, about 200 L; enzymatic activity 2.2 CHU per mL.

A first step of elution of chymosin bound to the separated ion exchanger was carried out by resuspending the ion exchanger in 20 L of 0.05M NaH$_2$PO$_4$ containing 10% (w/v) NaCl and at a pH adjusted to about 5.9 with 25% (w/v) ammonia water, under gentle stirring for about 10 minutes followed by filtration to obtain a first chymosin fraction having the following composition: volume, 20.2 L; weight 21.5 kg; gravity 1.064; enzymatic activity 121.8 CHU per mL.

The separated and eluted ion exchanger was resuspended in an other 200 L of the above filtrate under agitation for about 20 minutes followed by separation of the ion exchanger by filtration. The filtrate (the second pepsin fraction) was collected. This fraction had the following composition: volume, about 200 L; enzymatic activity 2.2 CHU/mL.

A second step of elution of chymosin bound to the separated ion exchanger was carried out by resuspending the ion exchanger in 40 L of 0.05M NaH$_2$PO$_4$ containing 10% (w/v) NaCl and at a pH adjusted to about 5.9 with 25% (w/v) ammonia water, under gentle stirring for about 8 minutes followed by filtration to obtain a second chymosin fraction having the following composition: Volume, 38.3 L; weight 40.8 kg; gravity 1.064; enzymatic activity 66.4 CHU per mL.

The above binding and elution steps were repeated twice essentially as described above, using at each elution step 30 L of the above elution buffer to give a third and a fourth chymosin fraction and a third and a fourth pepsin fraction, respectively.

These chymosin fractions had the following composition:

| | Chymosin fraction 3 | Chymosin fraction 4 |
|---|---|---|
| Volume | 32.0 L | 31.0 L |
| Weight | 34.0 kg | 33.0 |
| Gravity | 1.064 | 1.064 |
| Enzyme activity | 87.3 CHU per mL | 90.1 CHU per mL |

The resulting third and fourth pepsin fractions had the following compositions:

| | Pepsin fraction 3 | Pepsin fraction 4 |
|---|---|---|
| Volume | about 200 L | about 200 L |
| Enzyme activity | 2.28 CHU/mL | 2.28 CHU/mL |

The ion exchanger was finally washed by resuspension in 10 L of elution buffer and separated by filtration to give a washing liquor having the following composition: Volume, 9.7 L; weight 10.3 kg; gravity 1.064; enzymatic activity 15.2 CHU per mL.

The above four chymosin fractions and the above 9.7 L of washing liquor were combined and analyzed to give the following composition: Total volume, 131.2 L; enzymatic activity 77 CHUs/mL.

Correspondingly, the four above pepsin fractions were combined to give the following composition: Weight 837 kg; volume 834 L; gravity 1.003 kg/L; enzymatic activity 2.2 CHU/mL; total activity 1.83 MCHU.

3. Salting of combined chymosin fractions

The combined chymosin fractions were salted gently until 19° Be followed by the addition of 0.5% (w/v) Na-benzoate, and pH was adjusted to 5.6 to 5.7.

4. Filtration

The above salted chymosin fractions were filtered using a two-step filtration step. First, about 1 w/v % of perlite filtering material was added to the solution and the mixture was transferred to a filtering nutsch. Secondly, the filtrate resulting from the first filtration step was filtered by means of a sterile-filter plate (Seitz EK).

The combined EK-filtered chymosin eluates had the following compositions: volume, about 140 L, enzymatic activity (strength) of 72.8 CHU/mL. The total activity was 10.2 MCHU. Of the total enzymatic activity 98.4% was chymosin and 1.6% was pepsin according to the modified Garnot procedure whereas only 0.16% was bovine pepsin according to the RIE method.

TABLE 4.1

Calculations of yield, % MCHU relative to the enzymatic activity of the crude extract

|  | litres | CHU/mL | MCHU | Yield |
|---|---|---|---|---|
| Starting material | 800 | 14.9 | 11.9 | 100 |
| Chymosin eluates | 131 | 77.0 | 10.1 | 84.9 |
| EK-filtrates | 140 | 72.8 | 10.2 | 85.7 |
| Pepsin fractions | 800 | 2.2 | 1.8 | 15.1 |

The enzymatic yield obtained in the EK-filtered chymosin fractions and the pepsin fractions relative to the starting material was 100.8%.

Example 5

The preparation of a high concentrate ion-exchange calf rennet in semi-industrial scale The above procedure was repeated with 646 L of the crude extract filtrate+wash as described above, with the following exception:

The cation exchanger was suspended in about 3×200 L of crude extract filtrate+wash, followed by elution with 3×about 1 L of elution buffer. Finally, the cation exchanger was washed with 3×about 1 L of elution buffer.

TABLE 5.1

Calculations of yield, % MCHU relative to the enzymatic activity of the crude extract

|  | litres | CHU/mL | MCHU | Yield |
|---|---|---|---|---|
| Starting material | 600 | 14.6 | 8.76 | 100 |
| 1. chymosin eluate | 1.050 | 1295 | 1.36 |  |
| 2. chymosin eluate | 1.235 | 1665 | 2.06 |  |
| 3. chymosin eluate | 1.050 | 1923 | 2.02 |  |
| 1. wash | 1.075 | 1181 | 1.27 |  |
| 2. wash | 1.050 | 234 | 0.25 |  |
| 3. wash | 1.025 | 26 | 0.03 |  |
| Combined chymosin fractions |  |  | 6.99 | 79.8 |
| Pepsin fractions | 614 | 2.7 | 1.66 | 18.9 |

The enzymatic yield obtained in the two fractions relative to the starting material was 99.7%.

The concentrated product with a concentration of 1500 to 2000 CHU/mL will be suitable for a subsequent production of a powdered rennet product.

Example 6

The preparation of purified fractions of chymosin and bovine pepsin from aqueous extracts of calf stomachs An aqueous rennet extract of calf stomachs prepared essentially as described in Example 4 was activated at pH 2 for one hour and centrifuged afterwards, also essentially as described in Example 4. The filtrate was adjusted to pH 2.0 and subsequently assayed for milk clotting activity and enzyme composition according to the above analytical methods.

To a volume of 100 liters of this primary filtrate was added 1.0 kg of Whatman® SE 53 ion exchanger. The enzymes present in the filtrate was allowed to adsorb to the ion exchanger for about 20 minutes under gentle stirring after which the ion exchanger was separated from the ion exchanger-filtrate mixture by means of a filtration step according to the method as defined in Example 4. The separated ion exchange material was washed with 2 liters of deionized water at pH 2.0.

The above secondary filtrate, assumingly containing the bovine pepsin was collected and the pH was adjusted to 6.0 with sodium hydroxide solution The separated ion exchanger was eluted with 20 liters of elution buffer A (10% (w/v) NaCl, 50 mM sodium phosphate buffer at pH 5.9) for 10 minutes under gentle stirring. Following this elution, the ion exchanger was filtered off and the filtrate assumingly containing the chymosin fraction of the starting aqueous extract, was collected.

The ion exchanger was now mixed with a further volume of 100 liters of the above primary filtrate, separated from the mixture and eluted in the same manner as described above. In this manner the ion exchanger was contacted a total of 6 times with volumes of 100 liters of primary filtrate, respectively. For the last 3 elution steps, a little change in elution volume was made. Instead of 20 liters of elution buffer A only 10 liters were used to elute the enzymes from the separated ion exchanger. Following the repeated contacts, the ion exchange material was washed twice with 2 liters of elution buffer A for 10 minutes. The six chymosin fractions including the washing fractions were mixed. The fractions were assayed for milk clotting activity and enzyme composition The results from this cation exchange process are summarized in Table 6.1 below.

Following each of the above repeated cation exchange contacts secondary filtrates assumingly containing the pepsin fraction were obtained as described above. Anion exchange processing was now performed on each of these filtrates in the following manner: to each volume of 84 liters of secondary filtrate was added 0.75 kg Whatman® DE 53 anion exchanger to give a secondary filtrate-anion exchanger mixture, and the pepsin was allowed to adsorb to the ion exchanger for 20 minutes under gentle stirring after which the ion exchanger was separated from the mixture by means of filtration essentially as described in Example 4 to give a waste filtrate fraction. The separated ion exchanger was washed with 2 liters of deionized water at pH 6.0. The waste fraction i.e. the above filtrate resulting from the above separation, was assayed for milk clotting activity. The ion exchanger was eluted with 5 liters of elution buffer B (10% w/v NaCl, 50 mM sodium phosphate buffer at pH 5.5) for 10 minutes under gentle stirring. Following the elution, the ion exchanger was filtered off and the purified bovine pepsin-containing filtrate was collected.

The ion exchanger was then mixed with a further volume of 84 liters of the above secondary filtrate, separated from the mixture and eluted in the same manner as described above. In this manner, the ion exchanger was contacted a total of 7 times with 84 liters of secondary filtrate, respectively. Following the repeated contacts, the ion exchange material 25 was washed once with 2 liters of elution buffer B for 10 minutes. The seven pepsin-containing fractions including the washing fraction were mixed and the combined fraction was assayed for milk clotting activity and enzyme composition according to the above analytical methods. The results from this anion exchange process are summarized in the below Table 6.1.

To the resulting combined eluted chymosin and bovine pepsin solutions NaCl was added to 18° B for commercial food grade liquid rennets or for further downstream processing use.

TABLE 6.1

Milk clotting activity of partially purified extract of calf stomachs (starting material), eluates from cation exchange (chymosin fraction), eluates from anion exchange (isolated bovine pepsin fraction) and waste fraction from anion exchange

| Ion exchange | Description | Volume l | Milk clotting activity CHU/ ml | Total enzyme content MCHU | Enzyme composition % chymosin | Yield % |
|---|---|---|---|---|---|---|
| | Starting material | 590 | 10.7 | 6.31 | 85 | 100 |
| Cation exchange | Chymosin fraction | 91 | 55.5 | 5.05 | 100 | 80 |
| Anion exchange | Isolated bovine pepsin fraction | 37 | 31.2 | 1.15 | 39 | 18 |
| | Waste fraction | 580 | 0.1 | 0.06 | | 1 |

[1] 1 MCHU = 1,000,000 CHU

The enzymatic yield obtained in the combined chymosin fraction, the combined bovine pepsin fraction and the waste fraction relative to the starting material was 99%

Example 7

Improvement of the stability of rennet compositions by the addition of stabilizing agents a. The effect of an oxidizing agent on the milk clotting activity of rennets with different contents of impurities Selected rennet compositions were subjected to an oxidation treatment comprising diluting the compositions to a strength of 4 CHUs/mL in distilled water (reference dilution) and in distilled water containing 20 ppm of chloramine T. The dilutions were left at room temperature for 60 minutes before measuring the milk clotting activity of each dilution. The residual activity was calculated for the chloramine-containing solution relative to the activity of the reference dilution. The selected rennet compositions included a non-purified rennet composition prepared by a conventional extraction method according to a procedure as described above (bovine rennet, Chr. Hansen's Laboratorium), a partially purified (precipitated) calf rennet composition (P-99, Boll, France) and a fermentation produced chymosin (FPC) product expressed in an Aspergillus sp. (Chr. Hansen's Laboratorium). No stabilizing agents were added to any of these three product samples. The results are summarized in Table 7.1.

TABLE 7.1

Residual milk clotting activity of bovine rennet, partially purified calf rennet and fermentation produced chymosin (%)

| | |
|---|---|
| Bovine rennet | 97 |
| Calf rennet, P-99 | 55 |
| FPC | 10 |

These results clearly illustrate that rennets having a reduced or a low content of impurities are susceptible to oxidizing agents and that their milk clotting activity is drastically impaired by contact with such agents.

b. The effect of selected compounds on the stability of purified rennet compositions A FPC rennet composition expressed in an Aspergillus sp. was subjected to the above contact with chloramine with and without addition of a compound to be tested for possible protecting effect against the destabilizing effect of the chloramine. The results are summarized in Table 7.2:

TABLE 7.2

The milk clotting activity stabilizing effect of selected compounds

| Compound added | Residual activity (%) |
|---|---|
| None | 14 |
| 2% sodium citrate | 15 |
| 2% casamino acids | 84 |
| 0.5% tryptophan | 27 |
| 0.5% phenylalanine | 44 |
| 0.5% tyrosine | 14 |
| 0.5% L-methionine | 99 |
| 1% whey protein | 53 |
| 1% bovine albumin | 29 |
| 2% sodium ascorbate | 96 |
| 2% casein peptone | 98 |
| 0.5% cysteic acid | 98 |
| 0.25% DL methionine | 97 |
| 0.25% L-methionine | 98 |

The tested rennet composition was fermentation produced chymosin containing about 100 CHU/mL.

Example 8

The effect of methionine as a stabilizing agent to retain the milk clotting activity of rennet compositions contacted with oxidizing agents In this experiment a chymosin-containing eluate (a partially purified rennet composition) from Example 4 was contacted with chloramine T as described in Example 7, with and without the presence of methionine. The initial and residual milk clotting activity was determined according to the method as defined above. The results are summarized in Table 8.1:

TABLE 8.1

The stabilizing effect of methionine on the milk clotting activity in a partially purified (ion exchanged) rennet composition contacted with 20 ppm chloramine T

| Methionine, wt % | Residual activity, % |
|---|---|
| 0.0 | 55 |
| 0.023 | 87 |
| 0.045 | 90 |
| 0.050 | 95 |
| 0.057 | 95 |
| 0.068 | 97 |
| 0.091 | 100 |
| 0.102 | 99 |
| 0.170 | 100 |
| 0.283 | 96 |
| 0.566 | 99 |

These results illustrate that a partially purified rennet composition prepared by the cation exchange process as described herein can be effectively stabilized against the destabilizing effect of a strong oxidizing agent such as chloramine T by the addition of small amounts of methionine.

Example 9

Preparation of purified fractions of chymosin and bovine pepsin from aqueous extracts of calf stomachs An aqueous rennet extract of calf stomachs was activated at pH 2 for one hour and subsequently filtered. The filtrate was adjusted to pH 2.0 and assayed for milk clotting activity and enzyme composition according to the above analytical methods. The conductivity was measured to be 23.6 mS/cm. To a volume of 500 mL of this primary filtrate 10 g of Whatman® SE 53 cation exchanger was added. Adsorption of enzymes to the ion exchanger was performed for 20 minutes under gentle stirring after which the ion exchanger was separated from the ion exchanger-filtrate mixture by a filtration step.

The resulting secondary filtrate, assumingly containing the bovine pepsin was collected and the pH was adjusted to 6.0 with sodium hydroxide solution. The filtrate was assayed for milk clotting activity.

The ion exchanger was now mixed with a further volume of 500 mL of the above primary filtrate, adsorption was allowed to take place for 20 minutes and the ion exchanger was finally separated from the mixture in the same manner as described above.

The separated ion exchanger was then eluted with 60 mL of elution buffer A [10% (w/v) NaCl, 50 mM sodium phosphate buffer at pH 5.9] for 10 minutes under gentle stirring. Following this elution, the ion exchanger was filtered off and the filtrate, assumingly containing the chymosin fraction of the starting aqueous extract, was collected. The filtration was followed by a short rinse of the ion exchanger on the filter with 10 mL of elution buffer A. 69 mL chymosin-containing fraction was collected. The ion exchanger was washed once with 60 mL of elution buffer A for 10 minutes. The fractions were assayed for milk clotting activity. The results from this cation exchange process are summarized in Table 9.1 below.

Following the repeated cation exchange contacts, secondary filtrates assumingly containing the pepsin fraction were collected as described above. A volume of 100 mL was taken out for analytical use. Anion exchange processing was now performed on both of these filtrates in the following manner: to the first 450 mL of secondary filtrate was added 10 g Whatman® DE 53 anion exchanger to give a secondary filtrate-anion exchanger mixture, and the pepsin was allowed to adsorb to the ion exchanger for 20 minutes under gentle stirring after which the ion exchanger was separated from the mixture by a filtration step as described above to give a waste filtrate fraction.

The ion exchanger was then mixed with a further volume of the 450mL of the above secondary filtrate, adsorption was allowed to take place for 20 minutes and the ion exchanger was finally separated from the mixture in the same manner as described above. The two waste fractions were collected and assayed for milk clotting activity.

The separated ion exchanger was then eluted with 110 mL of elution buffer B [10% (w/v) NaCl, 50 mM sodium phosphate buffer at pH 5.5] for 10 minutes under gentle stirring. Following the elution, the ion exchanger was filtered off and the purified bovine pepsin-containing filtrate was collected. The filtration was followed by a short rinse of the ion exchanger on the filter with 10 mL of elution buffer B. 120 mL of pepsin-containing fraction were collected. The ion exchanger was washed once with 60 mL of elution buffer B for 10 minutes. The fractions were assayed for milk clotting activity. The isolated bovine pepsin fraction was also tested for enzyme composition. The results of this anion exchange process are summarized in Table 9.1 below.

TABLE 9.1

Milk clotting activity of partially purified extract of calf stomachs (starting material), eluates from cation exchange (chymosin fraction), eluates from anion exchange (isolated bovine pepsin fraction) and waste fraction from anion exchange

| Ion exchange | Description | Volume ml | Milk clotting activity CHU/ml | Total enzyme content CHU | Enzyme composition % chymosin | Yield % |
|---|---|---|---|---|---|---|
| | Starting material | 1000 | 10.5 | 10,500 | 74 | 100 |
| Cation exchange | Chymosin fraction | 69 | 100.0 | 6,900 | | 66 |
| | Wash of SE 53 | 59 | 7.7 | 454 | | 4 |
| | Secondary filtrates[1] | 1000 | 2.9 | 2,900 | | |
| Anion exchange | Isolated bovine pepsin fraction | 120 | 24.9 | 2,988 | <5 | 29 |
| | Wash of DE 53 | 58 | 2.1 | 122 | | 1 |
| | Waste fractions | 900 | 0.1 | 90 | | 1 |

[1]100 mL of the 1000 mL secondary filtrate was taken out for analytical purposes corresponding to 3% of the yield The enzymatic yield obtained in the chymosin fractions, the pepsin fractions and the waste fractions relative to the starting material was 103% including the little portion for analysis.

Example 10

Preparation of purified fractions of chymosin and bovine pepsin from aqueous extracts of bovine stomachs An aqueous rennet extract of bovine stomachs was activated at pH 2 for one hour and filtered. The filtrate was adjusted to pH 2.0 and subsequently assayed for milk clotting activity and enzyme composition according to the above analytical methods. The conductivity was measured to be 11.1 mS/cm. To a volume of 2500 mL of this primary filtrate 75 g of Whatman® SE 53 cation exchanger was added. Adsorption of enzymes to the ion exchanger was performed for 20 minutes under gentle stirring after which the ion exchanger was separated from the ion exchanger-filtrate mixture by a filtration step.

The above secondary filtrate, assumingly containing the bovine pepsin was collected and the pH was adjusted to 6.0 with sodium hydroxide solution. The filtrate was assayed for milk clotting activity.

The separated ion exchanger was mixed with a further volume of 2500 mL of the above primary filtrate, adsorption was allowed to take place for 20 minutes and the ion exchanger was finally separated from the mixture in the same manner as described above.

The separated ion exchanger was then eluted with 245 mL of elution buffer A [10% (w/v) NaCl, 50 mM sodium phosphate buffer at pH 5.9] for 10 minutes under gentle stirring. Following this elution, the ion exchanger was filtered off and the filtrate assumingly containing the chymosin fraction of the starting aqueous extract, was collected. The filtration was followed by a short rinse of the ion exchanger on the filter with 25 mL of elution buffer A. 270 ml chymosin fraction was collected. The ion exchanger was washed once with 270 mL of elution buffer A for 10 minutes.

finally separated from the mixture in the same manner as described in Example 9. The two waste fractions were collected and assayed for milk clotting activity.

The separated ion exchanger was eluted with 225 mL of elution buffer B [10% (w/v) NaCl, 50 mM sodium phosphate buffer at pH 5.5] for 10 minutes under gentle stirring. Following the elution, the ion exchanger was filtered off and the purified bovine pepsin-containing filtrate was collected. The filtration was followed by a short rinse of the ion exchanger on the filter with 25 mL of elution buffer B. 245 mL of pepsin-containing fraction were collected. The ion exchanger was washed twice with 260 mL of elution buffer B for 10 minutes. The fractions were assayed for milk clotting activity. The isolated bovine pepsin-containing fraction was also tested for enzyme composition. The results from this anion exchange process are summarized in Table 10.1 below.

TABLE 10.1

Milk clotting activity of partially purified extract of bovine stomachs (starting material), eluates from cation exchange (chymosin fraction), eluates from anion exchange (isolated bovine pepsin fraction) and waste fraction from anion exchange

| Ion exchange | Description | Volume ml | Milk clotting activity CHU/ml | Total enzyme content CHU | Enzyme composition % chymosin | Yield % |
|---|---|---|---|---|---|---|
| | Starting material | 5000 | 4.9 | 24,500 | <24 | 100 |
| Cation exchange | Chymosin fraction | 270 | 7.9 | 2,133 | 83 | 9 |
| | Wash of SE 53 | 265 | 0.2 | 53 | | 0 |
| | Secondary filtrates[1] | 4985 | 4.3 | 21,436 | | |
| Anion exchange | Isolated bovine pepsin fraction | 245 | 79.4 | 19,453 | <2 | 79 |
| | 1st wash of DE 53 | 260 | 12.4 | 3,224 | | 13 |
| | 2nd wash of DE 53 | 260 | 1.7 | 442 | | 2 |
| | Waste fractions | 4835 | 0.1 | 484 | | 2 |

[1]175 mL of the 4985 mL secondary filtrate was taken out for analytical purposes corresponding to 3% of the yield The fractions were assayed for milk clotting activity. The chymosin fraction was also tested for enzyme composition. The results from this cation exchange process are summarized in Table 10.1 below.

Following the repeated cation exchange contacts, secondary filtrates assumingly containing the pepsin fraction were collected as described above. A volume of 175 mL was taken out for analytical use. Anion exchange processing was now performed on both of these filtrates in the following manner: to the first 2400 mL of secondary filtrate 75 g Whatman® DE 53 anion exchanger was added to give a secondary filtrate-anion exchanger mixture, and the pepsin was allowed to adsorb to the ion exchanger for 20 minutes under gentle stirring after which the ion exchanger was separated from the mixture by a filtration step as described in Example 9 to give a waste filtrate fraction.

The ion exchanger was then mixed with a further volume of 2400 mL of the above secondary filtrate, adsorption was allowed to occur for 20 minutes and the ion exchanger was The total enzyme yield obtained in the chymosin fractions, the pepsin fractions and the waste fractions relative to the starting material was 108% including the little portion for analysis.

Example 11 pH profile for the adsorption step of the cation exchange process

An aqueous rennet extract of calf stomachs was activated at pH 2 for one hour and filtered. The filtrate was adjusted to pH 2.0 and subsequently assayed for milk clotting activity and enzyme composition according to the above analytical methods. The milk clotting activity was measured to be 11.8 CHU/ml and the filtrate was found to contain 74% chymosin. The conductivity was measured to be 14.5 mS/cm. To a volume of 400 mL of this primary filtrate 4 g of Whatman® SE 53 cation exchanger was added. Adsorption of enzymes to the ion exchanger allowed to take place for 20 minutes at 10 different pH values ranging from 0.5 to 5.0 (at intervals of 0.5) under gentle stirring. These pH values were obtained by the addition of either diluted HCl or diluted NaOH which resulted in a higher volume of the mixture than 400 mL. The ion exchanger was then separated from the ion exchanger-filtrate mixture by filtration.

The above secondary filtrates from each of these 10 experiments assumingly containing the bovine pepsin were collected and assayed for milk clotting activity.

The separated ion exchange materials from the above experiments were each eluted with 40 mL of elution buffer A for 10 minutes under gentle stirring. Following this elution, the ion exchanger was filtered off and the filtrate assumingly containing the chymosin fraction of the starting aqueous extract, was collected. All of the chymosin fractions were assayed for milk clotting activity. The results from this cation exchange study are summarized in Table 11.1 below.

TABLE 11.1

Milk clotting activity of partially purified extract of calf stomachs (starting material), eluates from cation exchange (chymosin fraction) and secondary filtrates (bovine pepsin fraction) for different pH values during the adsorption step

| pH at adsorption | Chymosin fraction ml | Milk clotting activity CHU/ml | Yield in chymosin fraction % | Secondary filtrate ml | Milk clotting activity CHU/ml | Yield in secondary filtrate % | Total yield % |
|---|---|---|---|---|---|---|---|
| 0.5 | 39 | 3.7 | 3.1 | 450 | 7.8 | 74.4 | 78 |
| 1.0 | 37 | 78.5 | 61.5 | 445 | 3.6 | 33.9 | 95 |
| 1.5 | 38 | 90.0 | 72.5 | 410 | 2.1 | 18.2 | 91 |
| 2.0 | 36 | 99.0 | 75.5 | 400 | 3.0 | 25.4 | 101 |
| 2.5 | 38 | 87.6 | 70.5 | 400 | 3.1 | 26.3 | 97 |
| 3.0 | 32 | 98.0 | 66.4 | 385 | 3.2 | 26.1 | 93 |
| 3.5 | 47 | 66.0 | 65.7 | 395 | 4.0 | 33.5 | 99 |
| 4.0 | 36 | 25.3 | 19.3 | 399 | 10.3 | 87.1 | 106 |
| 4.5 | 39 | 1.9 | 1.6 | 400 | 12.4 | 105.1 | 107 |
| 5.0 | 37 | 0.5 | 0.4 | 410 | 12.5 | 108.6 | 109 |

The above results show that the optimal pH for adsorption (binding) of chymosin is about 2.0 since the chymosin fraction assumingly containing almost pure chymosin has the highest milk clotting activity with 75.5% yield in the eluate and a total yield of 101%

We claim:

1. A process of separating milk clotting aspartic endopeptidases present in an extract of animal stomach tissue, comprising the steps of
    (i) preparing an aqueous extract of animal stomach tissue that contains the aspartic endopeptidases chymosin and pepsin, and/or their pro-enzymes, to obtain a one-phase, crude and particulate matter-containing extract comprising said endopeptidases,
    (ii) adjusting the pH in the extract to a value where the pro-enzymes are converted into active endopeptidases, and keeping the extract at this pH until the pro-enzymes are activated,
    (iii) separating particulate matter from the extract resulting from step (ii) to obtain a one-phase, partially purified aqueous extract containing the milk clotting endopeptidases essentially in their active forms,
    (iv) mixing the partially purified extract of step (iii) with an ion exchange resin under conditions where pseudochymosin and chymosin present in the extract, but not the pepsin also present, is bound to the resin,
    (v) separating the mixture of (iv) into the ion exchange resin with chymosin and pseudochymosin bound thereto and an extract fraction containing the pepsin also present in the partially purified extract resulting from step (iii),
    (vi) recovering, under conditions where essentially all pseudochymosin is converted into chymosin, the chymosin and pseudochymosin from the ion exchange resin into an aqueous medium to obtain a solution containing the chymosin and pseudochymosin present in the partially purified extract resulting from step (iii) as chymosin.

2. A process according to claim 1 wherein pH is adjusted in step (ii) to a value which is in the range of 0.5 to 5.0.

3. A process according to claim 2 wherein the pH is adjusted to a value which is in the range of 1.0 to 3.0.

4. A process according to claim 3 wherein the pH is adjusted to a value which is in the range of 1.5 to 2.5.

5. A process according to claim 1 wherein particulate matter is separated in step (iii) by filtration or centrifugation.

6. A process according to claim 1 wherein the ion exchange resin is a strong ion exchange resin having a constant charge within a pH range of 1 to 13.

7. A process according to claim 6 wherein the ion exchange resin has a high binding strength.

8. A process according to claim 7 wherein the ion exchange resin is a sulfoxyethyl (SE) ion exchanger.

9. A process according to claim 8 wherein the ion exchange resin is Whatman® SE 53 cation exchanger.

10. A process according to claim 1 wherein the weight ratio between the ion exchange resin and the extract being contacted therewith is in the range of 0.1:100 to 10:100.

11. A process according to claim 10 wherein the weight ratio between the ion exchange resin and the extract being contacted therewith is in the range of 0.5:100 to 5:100.

12. A process according to claim 1 wherein the partially purified extract resulting from step (iii) has a conductivity which is in the range of 1 µS/cm to 30 mS/cm.

13. A process according to claim 12 wherein the conductivity is in the range of 1 to 20 mS/cm.

14. A process according to claim 1 wherein a chymosin stabilizing agent is added to the crude or the partially purified aqueous extract or to the chymosin-containing preparation.

15. A process according to claim 14 wherein the stabilizing agent added is methionine.

16. A process according to claim 1 wherein the amount of chymosin activity in the resulting chymosin-containing preparation is increased relative to the crude extract resulting from step (ii) by a factor which is in the range of 2 to 10000.

17. A process according to claim 1 which comprises as a further step removal of water from the chymosin-containing solution resulting from step (vi) to obtain a chymosin-containing preparation which is at least partially dehydrated.

18. A process according to claim 17 wherein the partial dehydration is obtained by ultrafiltration of the chymosin-containing preparation resulting in a retentate containing the chymosin.

19. A process according to claim 18 which comprises the further step of drying the retentate to obtain a rennet powder.

20. A process according to claim 19 wherein a carrier substance is added to the retentate prior to drying.

21. A process according to claim 19 or 20 wherein the resulting rennet powder has a strength which is in the range of 100 CHU to 2000 CHU per g.

22. A process according to claim 1 wherein at least 90% of the milk clotting activity present in the solution resulting from step (vi) is chymosin activity.

23. A process according to claim 22 wherein at least 95% of the milk clotting activity is chymosin activity.

24. A process according to claim 1 which comprises the further step of contacting the pepsin-containing extract fraction resulting from step (v) with an ion exchange resin under conditions where substantially all of the pepsin is bound to the resin, and recovering the pepsin from the resin into an amount of a liquid medium which is less than the amount of extract fraction applied to the resin.

25. A process according to claim 17 or 18 which further comprises the addition of usual rennet additives to obtain a liquid concentrated rennet composition having a strength which is in the range of 50 CHUs/mL to 3000 CHUs/mL.

26. A liquid rennet composition in which at least 90% of the milk clotting activity is from chymosin, comprising an effective amount of a compound which protects the chymosin against oxidative reduction in enzymatic activity, whereby the composition retains at least 50% of its milk clotting activity when it is diluted in distilled water containing 20 ppm of chloramine T to an activity of 4 CHUs/mL and kept herein at room temperature for about 60 minutes.

27. A composition according to claim 26 wherein at least 75% of the activity is retained.

28. A composition according to claim 27 wherein at least 90% of the activity is retained.

29. A composition according to claim 26 wherein the protecting compound is selected from the group consisting of a protein, a peptide, an amino acid and ascorbic acid.

30. A composition according to claim 29 wherein the protecting agent is methionine.

31. A composition according to claim 30 which contains methionine in an amount which is in the range of 0.01 to 2 wt %.

32. A composition according to claim 26 which has a milk clotting activity which is in the range of 20 CHUs/mL to 3000 CHUs/mL.

33. A composition according to claim 26 wherein the chymosin is derived from a mammal stomach tissue.

34. A composition according to claim 26 wherein the chymosin is a fermentation produced chymosin expressed by a microbial cell.

35. A powdered rennet composition in which at least 90% of the milk clotting activity is from chymosin, comprising an effective amount of a compound which protects the chymosin against oxidative reduction-in enzymatic activity, whereby the composition retains at least 50% of its milk clotting activity when the composition is diluted in distilled water containing 20 ppm of chloramine T to an activity of 4 CHUs/mL and kept herein at room temperature for about 60 minutes.

36. A composition according to claim 35 wherein at least 75% of the activity is retained.

37. A composition according to claim 35 wherein at least 90% of the activity is retained.

38. A composition according to claim 35 wherein the protecting compound is selected from the group consisting of a protein, a peptide, an amino acid and ascorbic acid.

39. A composition according to claim 38 wherein the protecting compound is methionine.

40. A composition according to claim 39 which contains methionine in an amount which is in the range of 0.01 to 2 wt %.

41. A composition according to claim 35 which has a milk clotting activity of at least 100 CHUs/g.

42. A composition according to claim 41 which further comprises a carrier substance.

43. A composition according to claim 35 which has a milk clotting activity of at least 200 CHUs/g.

44. A composition according to claim 35 which has a milk clotting activity of at least 500 CHUs/g.

45. A composition according to claim 35 which has a milk clotting activity of at least 800 CHUs/g.

46. A composition according to claim 35 which has a milk clotting activity of at least 1000 CHUs/g.

* * * * *